US00RE34065E

United States Patent [19]

Wainberg et al.

[11] E Patent Number: Re. 34,065

[45] Reissued Date of Patent: Sep. 15, 1992

[54] HYPOCHLORITE: TERTIARY ALCOHOL DISINFECTANTS WITH REDUCED OFFENSIVE ODOR

[75] Inventors: Mark A. Wainberg, Montreal; Chiu-Ming Wong, Winnipeg, both of Canada

[73] Assignee: Kam Scientific Inc., Winnipeg, Canada

[21] Appl. No.: 547,772

[22] Filed: Jul. 3, 1990

Related U.S. Patent Documents

Reissue of:

[64] Patent No.: 4,839,079
Issued: Jun. 13, 1989
Appl. No.: 112,205
Filed: Oct. 22, 1987

[30] Foreign Application Priority Data

Oct. 24, 1986 [CA] Canada ..... 521327

[51] Int. Cl.[5] ..... A61L 2/18; A61L 9/01; C11D 7/26; C11D 7/54

[52] U.S. Cl. ..... 252/104; 252/95; 252/106; 252/170; 252/174.11; 252/187.25; 252/187.26; 252/187.27; 252/187.29; 252/DIG. 14; 424/76.9; 424/661; 514/724

[58] Field of Search ..... 252/95, 104, 106, 170, 252/174.11, 187.25, 187.26, 187.27, 187.29, DIG. 14; 424/76.9, 661; 514/724

[56] References Cited

U.S. PATENT DOCUMENTS

| | | | |
|---|---|---|---|
| 2,694,772 | 11/1954 | Katz | 260/453 |
| 4,113,645 | 9/1978 | DeSimone | 252/186.44 |
| 4,196,140 | 4/1980 | Lynch | 260/453 |
| 4,287,080 | 9/1981 | Siklosi | 252/104 |

OTHER PUBLICATIONS

CA 84(20):137622h.
CA 87(22):169574x.

*Primary Examiner*—Paul Lieberman
*Assistant Examiner*—A. Beadles-Hay
*Attorney, Agent, or Firm*—Irell & Manella

[57] ABSTRACT

This invention provides a novel disinfectant composition which is an aqueous solution containing hypochlorite ions, such as sodium hypochlorite, containing a tertiary aliphatic alcohol, such a tertiary-butanol. The alcohol acts as an odor masking agent and as a stabilizer for hypochlorite ions while itself possessing disinfecting properties. The composition is useful as a disinfectant.

2 Claims, No Drawings

HYPOCHLORITE: TERTIARY ALCOHOL DISINFECTANTS WITH REDUCED OFFENSIVE ODOR

Matter enclosed in heavy brackets [ ] appears in the original patent but forms no part of this reissue specification; matter printed in italics indicates the additions made by reissue.

This invention relates to a novel disinfectant composition and more particularly it relates to a novel disinfectant composition containing hypochlorite ions.

It is known that chlorine-based disinfectants such as those containing hypochlorite ions, for example sodium hypochlorite, are useful in destroying pathogens such as bacteria. These disinfectants suffer from the disadvantage that they have an offensive odour of chlorine and potential users of such disinfectants object to the smell of chlorine and thus such disinfectants tend not to be the disinfectant of choice.

We have now found, and herein lies our invention, that the offensive odour of an aqueous solution containing hypochlorite ions can be reduced by the addition of a particular odour masking ingredients.

According to the invention, as claimed herein, there is provided a novel aqueous solution containing hypochlorite ions wherein there is present a tertiary aliphatic alcohol.

As an example of an aqueous containing hypochlorite ions there may be mentioned an aqueous solution containing an alkali metal or an alkaline earth metal hypochlorite such as lithium, sodium, potassium, calcium or barium hypochlorite. The hypochlorite compound may be present to an extent of up to about 2% w/w of the solution. A preferred hypochlorite is sodium hypochlorite which may be present in a concentration of 0.5% w/w.

The tertiary aliphatic alcohol present in the novel aqueous hypochlorite solution may be a tertiary alcohol containing from 4 to 8 carbon atoms such as tertiary-butanol, 2,3-dimethyl-2,3-butanediol or 2,4-dimethyl-2,4-pentanediol. Of these tertiary aliphatic alcohols, a preferred alcohol is tertiary-butanol. The presence of a tertiary aliphatic alcohol is advantageous in that it not only acts as an odour masking agent but it also has biocidal activity in possessing mild disinfectant properties and it additionally functions as a stabilizer for hypochlorite ions.

As a further preferred feature of the invention there is provided an aqueous solution containing a compound providing hypochlorite ions, such as sodium, potassium, lithium or calcium hypochlorite, in the presence of a tertiary aliphatic alcohol, such as tertiary-butanol, 2,3-dimethyl-2,3-butanediol or 2,4-dimethyl-2,4-pentanediol, wherein for each 1 part by weight of said compound there is present from about 2 parts by weight to about 30 parts by weight of tertiary aliphatic alcohol, preferably from about 5 parts to about 15 parts by weight of tertiary aliphatic alcohol.

For example, an aqueous solution containing 1 part by weight of sodium hypochlorite may have present therein from about 2 parts by weight to about 30 parts by weight, preferably from about 5 parts to about 15 parts by weight, of tertiary-butanol, 2,3-dimethyl-2,3-butanediol or 2,4-dimethyl-2,4-pentanediol. A particularly useful aqueous solution is one containing about 1 part by weight of sodium hypochlorite and about 10 parts by weight of tertiary-butanol, 2,3-dimethyl-2,3-butanediol or 2,4-dimethyl-2,4-pentanediol.

The aqueous solution containing hypochlorite ions may optionally have present therein one or more additional ingredients. Thus, for example, the aqueous solution may also contain a synthetic organic detergent, such as sodium dodecyl sulphate. Thus, for example, for each part by weight of compound providing hypochlorite ions, such as sodium hypochlorite, there may be present from about 0.005 to about 0.1 part by weight, preferably about 0.02 part by weight, of synthetic organic detergent, such as sodium dodecyl sulphate.

The aqueous solution containing hypochlorite ions may also optionally have present therein one or more chlorine stable fragrances, such as a lemon fragrance or a pine fragrance. Such fragrances may be present in an amount such that for each part by weight of hypochlorite compound there is present from about 0.005 to about 0.2 part by weight of fragrance, preferably about 0.02 part by weight of fragrance, preferably a lemon fragrance.

The amount of fragrance may vary according to the strength and volume of the fragrance used. A weaker fragrance may be present to an extent of 0.2% w/w whereas a stronger fragrance may be present to an extent of 0.02% w/w. The synthetic organic detergent, such as sodium dodecyl sulphate, not only provides a cleaning power to the disinfectant but it also helps to dissolve or maintain the fragrance in solution. Since suitable fragrances mentioned above are usually oil-based fragrances, the synthetic organic detergent may be used to dissolve the fragrance prior to addition to the aqueous solution and thereafter it maintains the fragrance in solution. When a fragrance is present to an extent of from about 0.005 to about 0.2% w/w, the range of detergent may generally be from about 0.005 to about 0.01% w/w. Quantities of detergent in excess of this amount may be present to provide additional detergency to the solution.

Other optional ingredients may be present in the novel aqueous solution of the invention such as a chlorine stable colouring agent.

The novel aqueous solutions of this invention are useful in destroying pathogens including viruses, bacteria and fungi.

The invention is illustrated by, but not limited by, the following Examples in which the ingredients are given as percentages of parts by weight.

EXAMPLE 1

An aqueous solution is prepared containing 0.5% w/w of sodium hypochlorite and 5% w/w of tertiary-butanol. There is thus obtained a disinfectant solution having an acceptable masked chlorine odour compared with a corresponding 0.5% w/w sodium hypochlorite solution containing no tertiary-butanol.

The 0.5% w/w of sodium hypochlorite may be replaced by 0.5% w/w of potassium, lithium or calcium hypochlorite and there is likewise obtained a satisfactory and acceptable disinfectant solution.

The 5% w/w of tertiary-butanol may be replaced by 5% w/w of 2,3-dimethyl-2,3-butanediol or 2,4-dimethyl-2,4-pentanediol and there is likewise obtained a satisfactory and acceptable disinfectant solution.

EXAMPLE 2

An aqueous solution is prepared containing 0.5% w/w of sodium hypochlorite, 5% w/w of tertiary-butanol and 0.01% w/w of sodium dodecyl sulphate. There is thus obtained a disinfectant solution having an acceptable masked chlorine odour.

The 0.5% w/w of sodium hypochlorite may be replaced by 0.5% w/w of potassium, lithium or calcium hypochlorite and there is likewise obtained a satisfactory and acceptable disinfectant solution.

The 5% w/w of tertiary-butanol may be replaced by 5% w/w of 2,3-dimethyl-2m3-butanediol or 2,4-dimethyl-2,4-pentanediol and there is likewise obtained a satisfactory and acceptable disinfectant solution.

EXAMPLE 3

An aqueous solution is prepared containing 0.5% w/w of sodium hypochlorite and 2.5% w/w of tertiary-butanol, 2,3-dimethyl-2,3-butanediol or 2,4-dimethyl-2,4-pentanediol. There is thus obtained a disinfectant solution having an acceptable masked chlorine odour compared with a corresponding sodium hypochlorite solution containing no tertiary-butanol.

EXAMPLE 4

An aqueous solution is prepared containing 0.5% w/w of sodium hypochlorite and 7.5% w/w of tertiary-butanol, 2,3-dimethyl-2,3-butanediol or 2,4-dimethyl-2,4-pentanediol. There is thus obtained a disinfectant solution having an acceptable masked chlorine odour compared with a corresponding sodium hypochlorite solution containing no tertiary-butanol.

EXAMPLE 5

An aqueous solution is prepared containing the following ingredients:

0.5% w/w of sodium hypochlorite;
5.0% w/w of tertiary-butanol;
0.01% w/w of sodium dodecyl sulphate; and
0.01% w/w of lemon fragrance.

There is thus prepared an aqueous disinfectant solution which has an acceptable masked chlorine odour when used for its intended purpose of destroying pathogens.

The 0.5% w/w of sodium hypochlorite may be replaced by 0.5% w/w of potassium, lithium or calcium hypochlorite and there is likewise obtained a satisfactory and acceptable disinfectant solution.

The 5% w/w of tertiary-butanol may be replaced by 5% w/w of 2,3-dimethyl-2,3-butanediol or 2,4-dimethyl-2,4-pentanediol and there is likewise obtained a satisfactory and acceptable disinfectant solution.

The embodiments of the invention in which are exclusive property or privilege is claimed are defined as follows:

1. A stabilized disinfectant composition, comprising, in aqueous solution:

0.5% w/w of hypochlorite selected from the group consisting of sodium hypochlorite, lithium hypochlorite, potassium hypochlorite and calcium hypochlorite;
5.0% w/w of t-butanol;
0.01% w/w sodium dodecyl sulphate; and
0.01% w/w lemon fragrance.

2. The disinfectant composition of claim 1, comprising:

0.5% w/w sodium hypochlorite;
5.0% w/w tertiary-butanol;
0.01% w/w sodium dodecyl sulphate; and
0.01% w/w lemon fragrance.

* * * * *